(12) United States Patent
Kato et al.

(10) Patent No.: US 6,287,439 B1
(45) Date of Patent: Sep. 11, 2001

(54) GAS SENSOR

(75) Inventors: Nobuhide Kato, Ama-gun; Hiroshi Kurachi, Nagoya; Takeya Miyashita, Kasugai, all of (JP)

(73) Assignee: NGK Insulators, Ltd. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/079,206

(22) Filed: May 15, 1998

(30) Foreign Application Priority Data

May 20, 1997 (JP) .................................................. 9-130153

(51) Int. Cl.[7] .......................... G01N 27/409; G01N 27/41
(52) U.S. Cl. .......................... 204/425; 204/408; 204/426; 205/781; 219/209; 219/543
(58) Field of Search .................................... 204/424, 426, 204/408, 425; 205/784, 784.5, 785, 781; 219/209, 543

(56) References Cited

U.S. PATENT DOCUMENTS

| 4,708,777 | * | 11/1987 | Kuraoka | ............................. | 205/784.5 |
| 5,322,611 | | 6/1994 | Zaromb . | | |
| 5,547,552 | * | 8/1996 | Hasegawa et al. | .................. | 204/406 |
| 5,672,811 | * | 9/1997 | Kato et al. | ............................. | 204/425 |
| 5,902,469 | * | 5/1999 | Kato et al. | ............................. | 204/425 |
| 5,942,190 | * | 8/1999 | Kato et al. | ............................. | 422/98 |

FOREIGN PATENT DOCUMENTS

| 0 678 740 A1 | * | 10/1995 | (EP) . |
| 0 769 693 A1 | * | 4/1997 | (EP) . |
| 0 769 694 A1 | * | 4/1997 | (EP) . |
| 08-271476 | * | 10/1996 | (JP) . |
| 09-113484 | * | 5/1997 | (JP) . |

* cited by examiner

Primary Examiner—Robert J. Warden, Sr.
Assistant Examiner—Kaj K. Olsen
(74) Attorney, Agent, or Firm—Parkhurst & Wendel, L.L.P.

(57) ABSTRACT

A gas sensor is disclosed in order to decrease the offset value to a degree in which no trouble occurs in the measurement without causing any reduction of NOx so that the measurement accuracy for NOx is improved. In the gas sensor, NOx contained in a measurement gas introduced into a second chamber is decomposed by means of catalytic action and/or electrolysis to pumping-process oxygen produced by the decomposition so that NOx is measured on the basis of a pumping current flowing through a measuring pumping cell thereby. The gas sensor has the following pattern of a heater. That is, a minute pitch is provided for a pattern at a portion corresponding to the forward end of a sensor element, a coarse pitch is provided for a pattern at a central portion, and a pattern is removed at a portion corresponding to the backward end of the sensor element. Thus, the measuring pumping cell is allowed to have a resistivity of electronic conduction of not less than 1 MΩ after conversion into a resistance value.

7 Claims, 12 Drawing Sheets

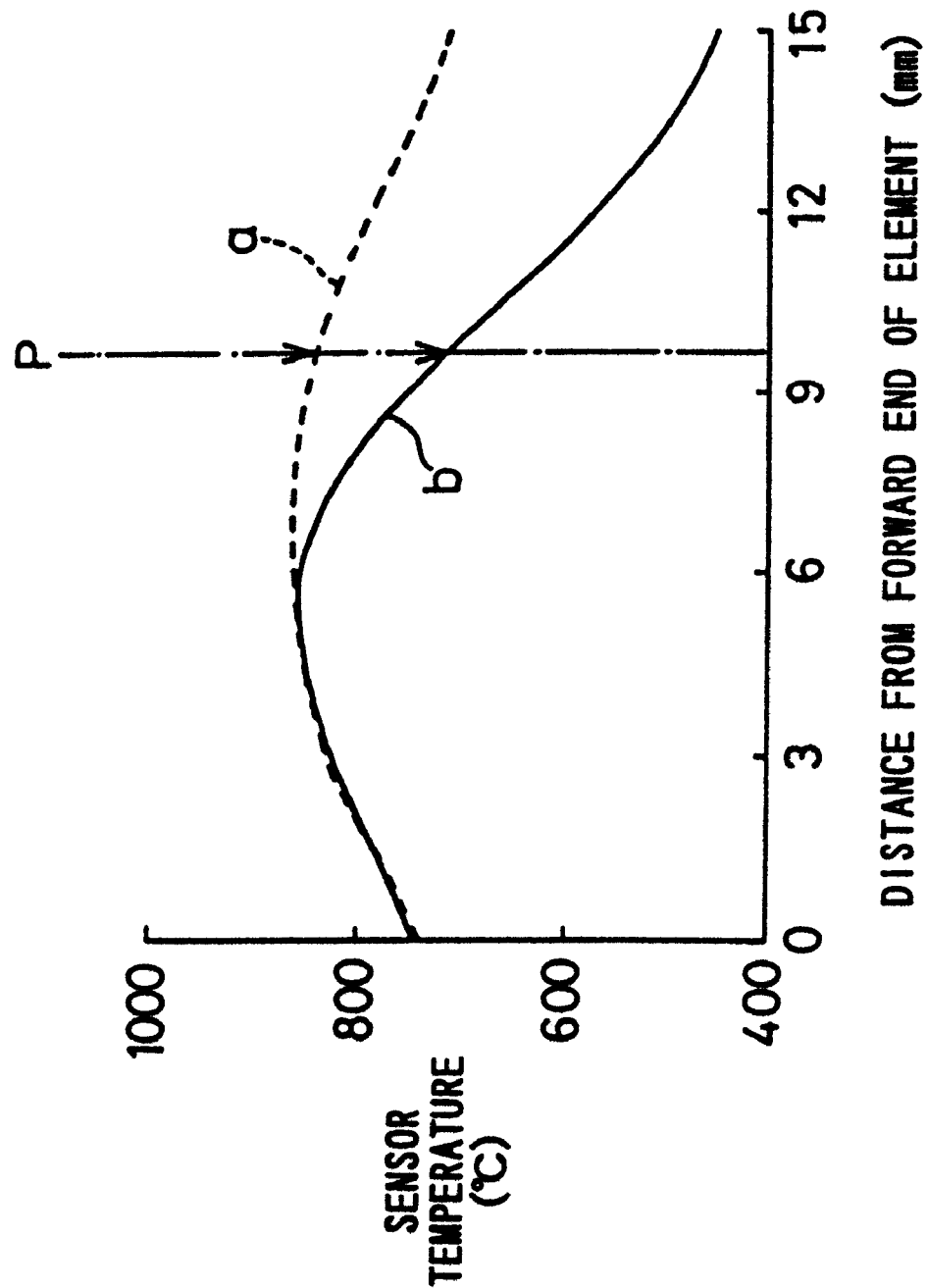

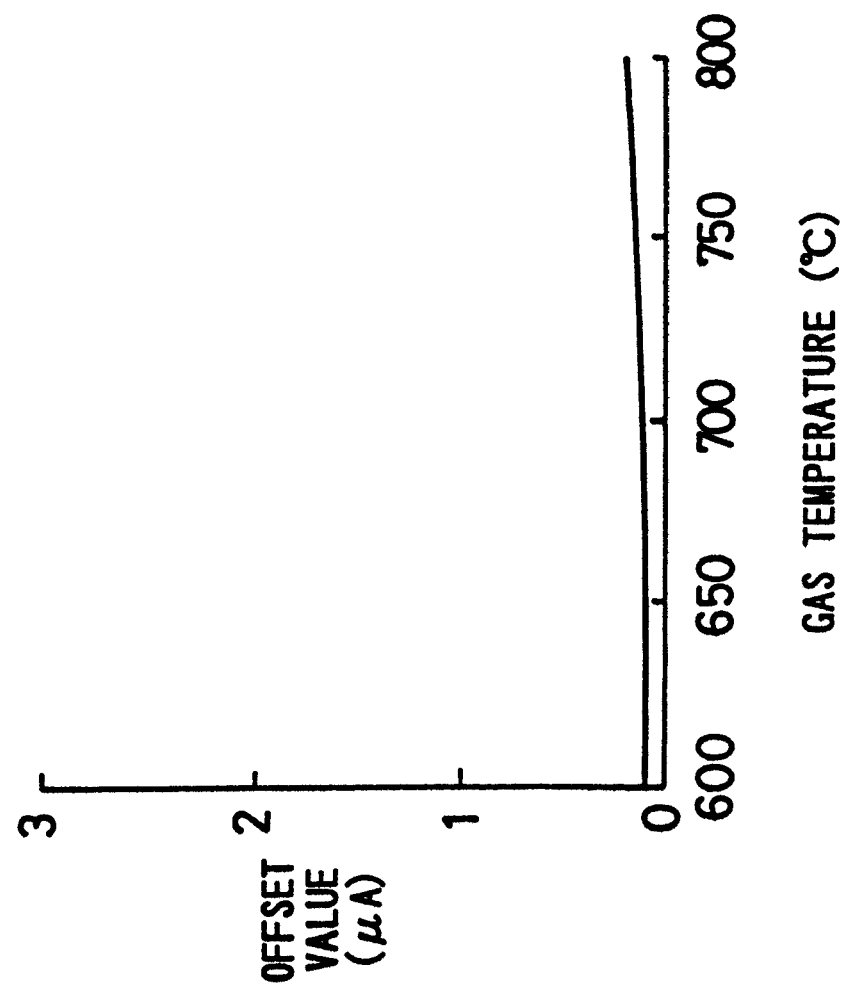

F I G. 12
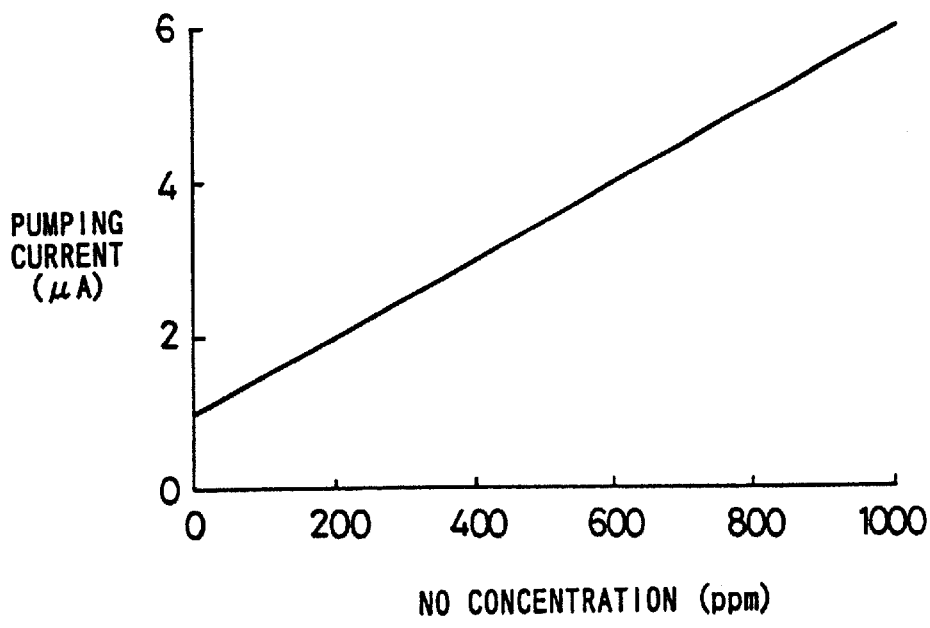
PRIOR ART

GAS SENSOR

BACKGROUND OF THE INVENTION

1. Field of the Invention

The present invention relates to a gas sensor for measuring gas components such as NO, $NO_2$, $SO_2$, $CO_2$, and $H_2O$ contained in, for example, atmospheric air and exhaust gas discharged from vehicles or automobiles.

2. Description of the Related Art

Exhaust gas, which is discharged from vehicles or automobiles such as gasoline-fueled automobiles and diesel powered automobiles, contains nitrogen oxides (NOx) such as nitrogen monoxide (NO) and nitrogen dioxide ($NO_2$), as well as carbon monoxide (CO), hydrocarbon (CH), hydrogen ($H_2$), oxygen ($O_2$) and so on. In such exhaust gas, about 80% of the entire NOx is occupied by NO, and about 95% of the entire NOx is occupied by NO and $NO_2$.

The three way catalyst, which is used to clean HC, CO, and NOx contained in the exhaust gas, exhibits its maximum cleaning efficiency in the vicinity of the theoretical air fuel ratio (A/F=14.6). If A/F is controlled to be not less than 16, the amount of produced NOx is decreased. However, the cleaning efficiency of the catalyst is lowered, and consequently the amount of discharged NOx is apt to increase.

Recently, in order to effectively utilize fossil fuel and avoid global warming, the market demand increases, for example, in that the discharge amount of $CO_2$ should be suppressed. In order to respond to such a demand, it becomes more necessary to improve the fuel efficiency. In response to such a demand, for example, the lean burn engine and the catalyst for cleaning NOx are being researched. Especially, the need for a NOx sensor increases.

A conventional NOx analyzer has been hitherto known in order to detect NOx as described above. The conventional NOx analyzer is operated to measure a characteristic inherent in NOx, based on the use of chemical luminous analysis. However, the conventional NOx analyzer is inconvenient in that the instrument itself is extremely large and expensive. The conventional NOx analyzer requires frequent maintenance because optical parts are used to detect NOx. Further, when the conventional NOx analyzer is used, any sampling operation should be performed for measurement of NOx, wherein it is impossible to directly insert a detecting element itself into a fluid. Therefore, the conventional NOx analyzer is not suitable for analyzing transient phenomena such as those occur in the exhaust gas discharged from an automobile, in which the condition frequently varies.

In order to dissolve the inconveniences as described above, there has been suggested and practically used a sensor for measuring a desired gas component in exhaust gas by using a substrate composed of an oxygen ion-conductive solid electrolyte.

FIG. 10 shows a cross-sectional arrangement of a gas sensor 10 disclosed in Japanese Laid-Open Patent Publication No. 8-271476.

The gas sensor 10 is operated as follows. That is, a measurement gas is introduced into a first hollow space 14 via a first diffusion rate-determining section 12. A first oxygen pumping means 22, which comprises an inner pumping electrode 16, a solid electrolyte 18, and an outer pumping electrode 20, is used to pump in or pump out oxygen contained in the measurement gas, into or from the first hollow space 14 to an extent that the measurement gas is not decomposed.

Subsequently, the measurement gas is introduced into a second hollow space 26 via a second diffusion rate-determining section 24. A second oxygen pumping means 36, which comprises a measurement gas-decomposing electrode 28 disposed in the second hollow space 26, a solid electrolyte 30, and a reference electrode 34 disposed in a reference gas-introducing space 32, is used to pump out oxygen produced by decomposition and electrolysis caused by the applied voltage or the catalytic action effected by the measurement gas-decomposing electrode 28.

The value of the current, which is required to pump out oxygen by the second oxygen pumping means 36, is measured to measure the predetermined gas component contained in the measurement gas, on the basis of the current value.

Those to which the gas sensor 10 is applicable include, for example, NOx sensors, $H_2O$ sensors and $CO_2$ sensors for measuring NOx, $H_2O$, and $CO_2$ in which the predetermined gas component has bound oxygen.

In the case of the use as a NOx sensor, NOx is catalytically decomposed by using, for example, Rh or Pt for the measurement gas-decomposing electrode 28. The oxygen produced during the decomposition can be detected as a pumping current, or it can be detected as a change in voltage of an oxygen concentration cell.

As shown in FIG. 11, another gas sensor 10A has been suggested (see, for example, Japanese Laid-Open Patent Publication No. 9-113484), in which the oxygen dependency of the gas sensor 10 described above is improved when the gas sensor 10 is used as a NOx sensor.

The gas sensor 10A comprises an auxiliary pumping electrode 38 disposed at a second hollow space 26. A third oxygen pumping means, i.e., an auxiliary pumping means 40 is constructed by the auxiliary pumping electrode 38, solid electrolytes (including 18 and 30), and a reference electrode 34. The oxygen, which diffuses and enters from a first hollow space 14 in a minute amount, is pumped out again by using the auxiliary pumping means 40. Accordingly, it is possible to greatly improve the measurement accuracy (especially the dependency on oxygen concentration).

However, the gas sensors 10, 10A are in the following actual state of affairs. That is, even when the oxygen concentration in the measurement gas is controlled to be, for example, not more than 1 ppm in the previous stage of NOx measurement by using the first oxygen pumping means 22, or by using the first oxygen pumping means 22 and the auxiliary pumping means 40, the pumping current value at NOx=0 (hereinafter referred to as "offset value") is a value corresponding to 100 ppm which is much higher than a value corresponding to 1 ppm.

If the offset value is always constant in all environments in which the gas sensors 10, 10A are used, no problem arises. However, it is feared that a large measurement error may be caused, because the offset value varies depending on the change in temperature of exhaust gas.

In order to decrease the offset value, it is conceived that strict control is performed by using the first oxygen pumping means 22, and strict control is performed by using the auxiliary pumping means 40, for example, so that the oxygen concentration to be controlled is further decreased. However, if such strict control is performed, a problem arises in that NOx is decomposed by the pumping process effected thereby.

FIG. 12 shows a situation of the problem described above. When the oxygen concentration in the first hollow space 14 of the gas sensor 10 shown in FIG. 10 is controlled to be $10^{-7}$ atm (about 300 mV as a voltage detected by an oxygen concentration detector), the offset value is 1.0 μA.

Theoretically and essentially, the offset value should be a value corresponding to a residual oxygen concentration in the first hollow space 14, i.e., 0.1 ppm (or corresponding to 0.2 ppm after conversion into a value of NO). However, the offset value is actually 1 μA (or a value of NO corresponding to 200 ppm obtained by conversion). The NO sensitivity is calculated in accordance with 5 μA/1000 ppm.

Therefore, if the offset value slightly changes depending on, for example, the temperature of the sensor element, and it is changed in a degree of 10%, then the resultant change corresponds to 20 ppm, which causes a serious problem when NOx is measured at a low concentration in a degree of several hundreds of ppm.

FIG. 13 shows such a situation. For example, when the temperature of the measurement gas (gas temperature) is changed by about 150° C. from 650° C. to 800° C., the offset value is changed in an amount of about 1.5 μA, i.e., 300 ppm. This causes a serious problem when NOx is measured at a low concentration of several hundreds of ppm.

In order to solve this problem, a method is conceived, in which the oxygen concentration in the first hollow space 14 is lowered. However, even when the oxygen concentration in the first hollow space 14 is lowered up to $10^{-10}$ atm, the offset value is still 1 μA. When the oxygen concentration is lowered up to $10^{-12}$ atm, the offset value is finally 0.1 μA (corresponding to 20 ppm). Under this condition, even when the offset value is changed by 2% due to the temperature change or the like, the amount of change is suppressed to be about 4 ppm at most, which is at a sufficient level to make measurement for several hundreds of ppm.

However, when the oxygen concentration in the first hollow space 14 is lowered to be too low, the reaction with NOx occurs in the first hollow space 14 before combustion of inflammable gas components such as HC and CO contained in exhaust gas. A new problem arises in that the decrease in sensitivity takes place.

SUMMARY OF THE INVENTION

The present invention has been made taking the foregoing problems into consideration, an object of which is to provide a gas sensor which does not cause any reduction of a predetermined gas component, which makes it possible to decrease the offset value to a degree in which no trouble occurs in measurement, and which makes it possible to improve the measurement accuracy for the predetermined gas component.

According to the present invention, there is provided a gas sensor comprising a main pumping means for pumping-processing oxygen contained in a measurement gas introduced from an external space into a processing space formed and comparted by solid electrolytes contacting with the external space so that a partial pressure of oxygen in the processing space is controlled to have a predetermined value at which a predetermined gas component contained in the measurement gas is not decomposable; and a measuring pumping means for decomposing a measurement gas component contained in the measurement gas after being pumping-processed by the main pumping means, by means of catalytic action and/or electrolysis so that oxygen produced by the decomposition is subjected to a pumping process; wherein the measurement gas component contained in the measurement gas is measured on the basis of a pumping current flowing through the measuring pumping means in accordance with the pumping process effected by the measuring pumping means; and the measuring pumping means has a resistivity of electronic conduction of not less than 1 MΩ after conversion into a resistance value.

According to the present invention, at first, the oxygen, which is contained in the measurement gas introduced from the external space, is pumping-processed by the main pumping means, and the oxygen is adjusted to have a predetermined concentration. That is, the partial pressure of oxygen in the processing space is controlled by the main pumping means to have the predetermined value at which the predetermined gas component contained in the measurement gas is not decomposable. The predetermined gas component includes, for example, NO. The measurement gas, which has been adjusted for the oxygen concentration by the aid of the main pumping means, is introduced into the detecting pumping means in the next step. The detecting pumping means decomposes the measurement gas component contained in the measurement gas after being pumping-processed by the main pumping means, by means of the catalytic action and/or the electrolysis. The oxygen produced by the decomposition is subjected to the pumping process. The pumping current is generated in the detecting pumping means in accordance with the amount of oxygen pumping-processed by the detecting pumping means. The measurement gas component corresponding to the amount of oxygen is measured on the basis of the generated pumping current. The measurement gas component includes, for example, NOx.

The measurement gas component is measured such that when the voltage is applied to the solid electrolyte, then the current flows in accordance with movement of oxygen ion, and the current is measured as a pumping current. During this process, when the measuring pumping means is at a high temperature, then the current flowing through the solid electrolyte originates not only from the oxygen ion, but the electronic conduction occurs although it is in an extremely minute amount. The electronic conduction appears as an offset value.

The electron conductivity is extremely small as compared with the conductivity of oxygen ion, and it is almost neglected in ordinary cases. However, when the concentration of an extremely minute amount of gas is measured, the limiting current is obtained only in a degree of about several μA. Therefore, the electronic conduction at the μA level serves as a large error factor. However, in the present invention, the resistivity of electronic conduction of the measuring pumping means is set to be not less than 1 MΩ after conversion into a resistance value. Therefore, it is possible to suppress the electronic conduction of the measuring pumping means. Accordingly, the offset value can be decreased, and thus the present invention is extremely useful to measure the measurement gas component at a low concentration.

As described above, it is approved that the electron conductivity of the measuring pumping means is not less than 1 MΩ after conversion into a resistance value. However, the electron conductivity of the measuring pumping means is preferably not less than 2 MΩ, and more preferably not less than 4 MΩ.

The gas sensor constructed as described above may further comprise an auxiliary pumping means including the solid electrolyte and an inner auxiliary pumping electrode and an outer auxiliary pumping electrode formed in contact with the solid electrolyte, for pumping out oxygen contained in the measurement gas after being pumping-processed by the main pumping means, toward the main pumping means.

In this embodiment, it is possible to pump out the oxygen contained in the measurement gas after being pumping-processed by the main pumping means, i.e., the oxygen which diffuses and enters in a minute amount. Therefore, it is possible to greatly improve the oxygen concentration dependency of the measuring pumping means. Thus, it is possible to improve the measurement accuracy.

The gas sensor constructed as described above may further comprise a heater for heating at least the main pumping means and the measuring pumping means to predetermined temperatures, and a heater control means for controlling electric power of the heater so that the temperature in the vicinity of the measuring pumping means is constant. In this embodiment, even when the temperature of the measurement gas is changed, it is easy to control the measuring pumping means to have a constant electron conductivity. Therefore, this embodiment is advantageous to measure the measurement gas component at a low concentration.

According to another aspect of the present invention, there is provided a gas sensor comprising a main pumping means for pumping-processing oxygen contained in a measurement gas introduced from an external space into a processing space formed and comparted by solid electrolytes contacting with the external space so that a partial pressure of oxygen in the processing space is controlled to have a predetermined value at which a predetermined gas component as a measurement objective is not decomposable; and a measuring pumping means for decomposing a measurement gas component contained in the measurement gas after being pumping-processed by the main pumping means, by means of catalytic action and/or electrolysis so that oxygen produced by the decomposition is subjected to a pumping process; wherein the measurement gas component contained in the measurement gas is measured on the basis of a pumping current flowing through the measuring pumping means in accordance with the pumping process effected by the measuring pumping means; the gas sensor further comprising a heater for heating at least the main pumping means and the measuring pumping means to predetermined temperatures, and a heater control means for controlling electric power of the heater so that the measuring pumping means has a constant impedance; wherein the measuring pumping means has a resistivity of electronic conduction which is set to be not less than a predetermined value.

According to this aspect of the present invention, the control is made to give a constant impedance between the electrodes between which the pumping current flows. That is, when the measuring pumping means is constructed by a detecting electrode exposed to the measurement gas after being pumping-processed by the main pumping means, a reference electrode formed at a reference gas-introducing space for introducing a reference gas thereinto, and the solid electrolyte intervening between the electrodes, the impedance between the detecting electrode and the reference electrode is measured to control the heater.

Alternatively, when the measuring pumping means is constructed by the detecting electrode, an electrode (for example, a main pumping outer electrode for constructing the main pumping means) other than the reference electrode, and the solid electrolyte intervening between the electrodes, and the pumping current is allowed to flow between the detecting electrode and the main pumping outer electrode while monitoring an electromotive force generated between the reference electrode and the detecting electrode, then the impedance between the detecting electrode and the main pumping outer electrode is measured to control the heater.

In the gas sensor according to the present invention, it is possible to decrease the width of variation of the offset value associated with the temperature change. Thus, it is possible to obtain the gas sensor having extremely high accuracy.

In the gas sensor according to the present invention, even when the temperature of the measurement gas is changed, the offset value can be controlled to be constant. Further, the resistivity of electronic conduction of the measuring pumping means is not less than 100 kΩ after conversion into a resistance value. Therefore, the gas sensor of the present invention is advantageous in that it is possible to sufficiently make allowance even when the electron conductivity is large to some extent.

The gas sensor constructed as described above may further comprise an auxiliary pumping means including the solid electrolyte and an inner auxiliary pumping electrode and an outer auxiliary pumping electrode formed in contact with the solid electrolyte, for pumping out oxygen contained in the measurement gas after being pumping-processed by the main pumping means, toward the main pumping means.

In this embodiment, it is possible to pump out the oxygen contained in the measurement gas after being pumping-processed by the main pumping means, i.e., the oxygen which diffuses and enters in a minute amount. Therefore, it is possible to greatly improve the oxygen concentration dependency of the measuring pumping means. Thus, it is possible to improve the measurement accuracy.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 4 shows characteristic curves illustrating temperature distributions in sensor elements before and after the improvement of the heater pattern;

FIG. 5 shows a characteristic curve illustrating variation of the offset value with respect to the change in gas temperature in the gas sensor according to the embodiment of the present invention;

FIG. 12 shows a characteristic curve illustrating the change in pumping current with respect to the change in NO concentration, obtained when the oxygen concentration in the first hollow space is controlled to be 0.1 ppm.

DESCRIPTION OF THE PREFERRED EMBODIMENTS

Explanation will be made below with reference to FIGS. 1 to 9 for illustrative embodiments in which the gas sensor according to the present invention is applied to gas sensors for measuring gas components such as NO, $NO_2$, $SO_2$, $CO_2$, and $H_2O$ contained in, for example, atmospheric air and exhaust gas discharged from vehicles or automobiles (hereinafter simply referred to as "gas sensor according to the embodiment").

Figure 1:
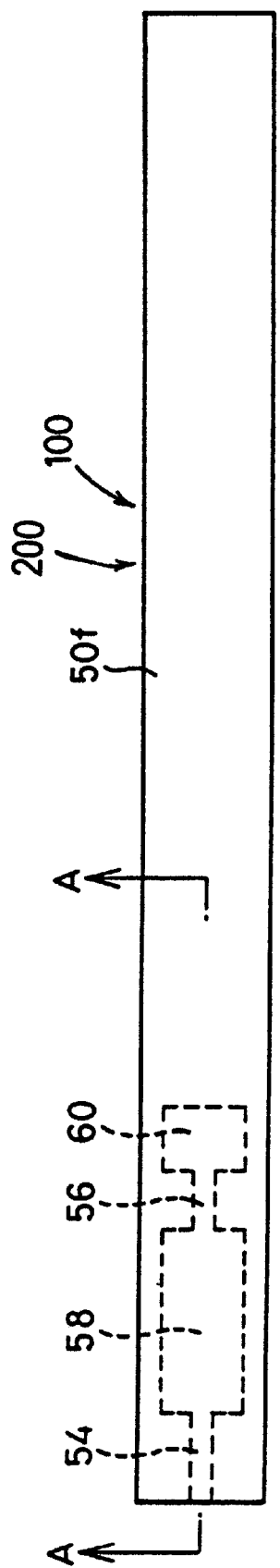
FIG. 1 shows a plan view illustrating a structure of a gas sensor according to an embodiment of the present invention.
Figure 2:
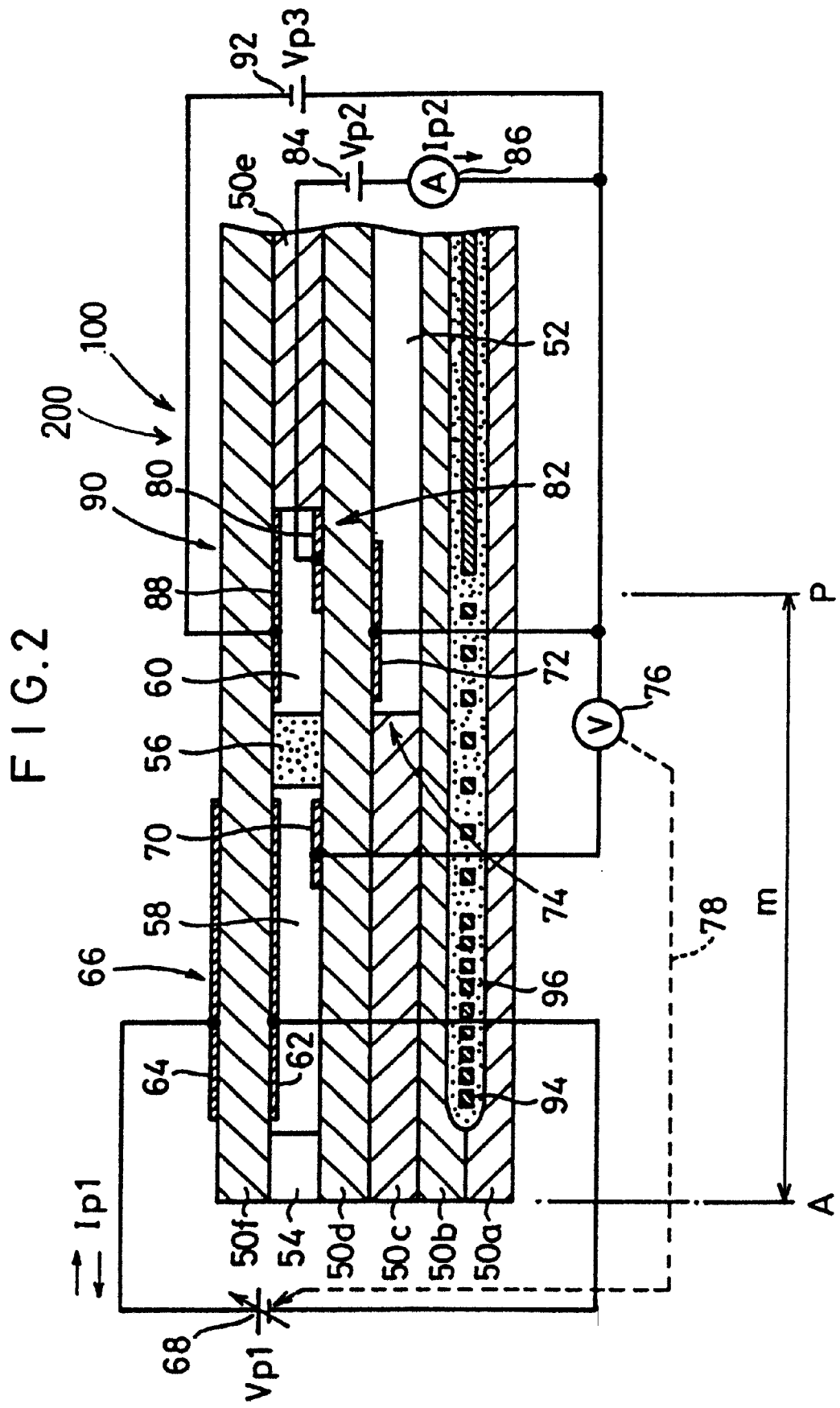
FIG. 2 shows a sectional view taken along a line A—A shown in FIG. 1.

As shown in FIGS. 1 and 2, a gas sensor 200 according to the embodiment of the present invention is generally constructed to have a lengthy plate-shaped configuration as a whole, comprising, for example, six stacked solid electrolyte layers 50a to 50f composed of ceramics based on the use of oxygen ion-conductive solid electrolytes such as $ZrO_2$. First and second layers from the bottom are designated as first and second substrate layers 50a, 50b respectively. Third and fifth layers from the bottom are designated as first and second spacer layers 50c, 50e respectively. Fourth and sixth layers from the bottom are designated as first and second solid electrolyte layers 50d, 50f respectively.

Specifically, the first spacer layer 50c is stacked on the second substrate layer 50b. The first solid electrolyte layer 50d, the second spacer layer 50e, and the second solid electrolyte layer 50f are successively stacked on the first spacer layer 50c. A space (reference gas-introducing space) 52, into which a reference gas such as atmospheric air to be used as a reference for measuring oxides is introduced, is formed between the second substrate layer 50b and the first solid electrolyte layer 50d, the space 52 being comparted by a lower surface of the first solid electrolyte layer 50d, an upper surface of the second substrate layer 50b, and side surfaces of the first spacer layer 50c.

The second spacer layer 50e is interposed between the first and second solid electrolyte layers 50d, 50f. First and second diffusion rate-determining sections 54, 56 are also interposed between the first and second solid electrolyte layers 50d, 50f.

A first chamber 58 for adjusting the partial pressure of oxygen in a measurement gas is formed and comparted by a lower surface of the second solid electrolyte layer 50f, side surfaces of the first and second diffusion rate determining sections 54, 56, and an upper surface of the first solid electrolyte layer 50d. A second chamber 60 for finely adjusting the partial pressure of oxygen in the measurement gas and measuring oxides such as nitrogen oxides (NOx) in the measurement gas is formed and comparted by a lower surface of the second solid electrolyte layer 50f, a side surface of the second diffusion rate-determining section 56, a side surface of the second spacer layer 50e, and an upper surface of the first solid electrolyte layer 50d.

The external space communicates with the first chamber 58 via the first diffusion-rate determining section 54, and the first chamber 58 communicates with the second chamber 60 via the second diffusion rate-determining section 56.

The first and second diffusion-rate determining sections 54, 56 give predetermined diffusion resistances to the measurement gas to be introduced into the first and second chambers 58, 60 respectively. Each of the first and second diffusion-rate determining sections 54, 56 can be formed as a passage composed of, for example, a porous material (for example, a porous member composed of $ZrO_2$), or a small hole having a predetermined cross-sectional area so that the measurement gas may be introduced. Alternatively, each of the first and second diffusion-rate determining sections 54, 56 may be constructed by a gap layer or a porous layer produced by printing. In this embodiment, the comparative magnitude does not matter between the respective diffusion resistances of the first and second diffusion rate-determining sections 54, 56. However, it is preferable that the diffusion resistance of the second diffusion rate-determining section 56 is larger than that of the first diffusion rate-determining section 54.

The atmosphere in the first chamber 58 is introduced into the second chamber 60 under the predetermined diffusion resistance via the second diffusion rate-determining section 56.

An inner pumping electrode 62 having a substantially rectangular planar configuration and composed of a porous cement electrode is formed on an entire lower surface portion for forming the first chamber 58, of the lower surface of the second solid electrolyte layer 50f. An outer pumping electrode 64 is formed on a portion corresponding to the inner pumping electrode 62, of the upper surface of the second solid electrolyte layer 50f. An electrochemical pumping cell, i.e., a main pumping cell 66 is constructed by the inner pumping electrode 62, the outer pumping electrode 64, and the second solid electrolyte layer 50f interposed between the both electrodes 62, 64.

A desired control voltage (pumping voltage) Vp1 is applied between the inner pumping electrode 62 and the outer pumping electrode 64 of the main pumping cell 66 by the aid of an external variable power source 68 to allow a pumping current Ip1 to flow in a positive direction or in a negative direction between the outer pumping electrode 64 and the inner pumping electrode 62. Thus, the oxygen in the atmosphere in the first chamber 58 can be pumped out to the external space, or the oxygen in the external space can be pumped into the first chamber 58.

A measuring electrode 70 having a substantially rectangular planar configuration and composed of a porous cement electrode is formed in the close vicinity of the second diffusion rate-determining section 56 on an upper surface portion for forming the first chamber 58, of the upper surface of the first solid electrolyte layer 50d. A reference electrode 72 is formed on a lower surface portion exposed to the reference gas-introducing space 52, of the lower surface of the first solid electrolyte layer 50d. An electrochemical sensor cell, i.e., a controlling oxygen partial pressure-measuring cell 74 is constructed by the measuring electrode 70, the reference electrode 72, and the first solid electrolyte layer 50d.

The controlling oxygen partial pressure-measuring cell 74 is operated such that the partial pressure of oxygen in the atmosphere in the first chamber 58 can be detected by measuring the electromotive force generated between the measuring electrode 70 and the reference electrode 72 by using a voltmeter 76, on the basis of the difference in oxygen concentration between the atmosphere in the first chamber 58 and the reference gas (atmospheric air) in the reference gas-introducing space 52.

That is, the voltage V, which is generated between the reference electrode 72 and the measuring electrode 70, is the electromotive force of the oxygen concentration cell generated on the basis of the difference between the partial pressure of oxygen of the reference gas introduced into the reference gas-introducing space 52 and the partial pressure of oxygen of the measurement gas in the first chamber 58. The voltage V has the following relationship known as the Nernst's equation.

$$V = RT/4F \cdot \ln(P_1(O_2)/P_0(O_2))$$

R: gas constant;
T: absolute temperature;
F: Faraday constant;
$P_1(O_2)$: partial pressure of oxygen in the first chamber 58;
$P_0(O_2)$: partial pressure of oxygen of the reference gas.

Therefore, the partial pressure of oxygen in the first chamber 58 can be detected by measuring the voltage V based on the Nernst's equation by using the voltmeter 76.

The detected value of the partial pressure of oxygen is used to control the pumping voltage Vp1 of the variable power source 68 by the aid of a feedback control system 78. Specifically, the pumping operation effected by the main pumping cell 66 is controlled so that the partial pressure of oxygen in the atmosphere in the first chamber 58 has a predetermined value which is sufficiently low to make it possible to perform the control of the partial pressure of oxygen in the second chamber 60 in the next step.

Each of the inner pumping electrode 62 and the outer pumping electrode 64 of the main pumping cell 66 and the measuring electrode 70 of the controlling oxygen partial pressure-measuring cell 74 is composed of an inert material having a low catalytic activity on NOx, for example, NO contained in the measurement gas introduced into the gas sensor.

Especially, each of the inner pumping electrode 62 and the measuring electrode 70 may be composed of a porous cement electrode. In this embodiment, each of the electrodes is composed of a metal such as Pt and a ceramic such as $ZrO_2$. It is necessary to use a material which has a weak reducing ability or no reducing ability with respect to the NO component in the measurement gas, for the inner pumping electrode 62 and the measuring electrode 70 disposed in the first chamber 58 to make contact with the measurement gas. It is preferable that each of the inner pumping electrode 62 and the measuring electrode 70 is composed of, for example, a compound having the perovskite structure such as $La_3CuO_4$ a cement comprising a ceramic and a metal such as Au having a low catalytic activity, or a cement comprising a ceramic, a metal of the Pt group, and a metal such as Au having a low catalytic activity. When an alloy composed of Au and a metal of the Pt group is used as an electrode material, it is preferable to add Au in an amount of 0.03 to 35% by volume of the entire metal component.

Further, a detecting electrode 80 having a substantially rectangular planar configuration and composed of a porous cermet electrode is formed on an upper surface portion for forming the second chamber 60, of the upper surface of the first solid electrolyte layer 50d. An electrochemical pumping cell, i.e., a measuring pumping cell 82 is constructed by the detecting electrode 80, the inner pumping electrode 62 of the main pumping cell 66, the first solid electrolyte layer 50d, the second spacer layer 50e, and the second solid electrolyte layer 50f.

The detecting electrode 80 is composed of, for example, a porous cermet comprising Rh as a metal capable of reducing NOx as the measurement gas component and zirconia as a ceramic. Accordingly, the detecting electrode 80 functions as a NOx-reducing catalyst for reducing NOx existing in the atmosphere in the second chamber 60. Further, when a measuring voltage Vp2 is applied between the detecting electrode 80 and the reference electrode 72 by the aid of a DC power source 84, the oxygen in the atmosphere in the second chamber 60 can be pumped out to the reference gas-introducing space 52. The pumping current Ip2, which flows in accordance with the pumping action of the measuring pumping cell 82, is detected by an ammeter 86.

On the other hand, an auxiliary pumping electrode 88 having a substantially rectangular planar configuration and composed of a porous cermet electrode is formed on an entire lower surface portion for forming the second chamber 60, of the lower surface of the second solid electrolyte layer 50f. An auxiliary electrochemical pumping cell, i.e., an auxiliary pumping cell 90 is constructed by the auxiliary pumping electrode 88, the second solid electrolyte layer 50f, the second spacer layer 50e, the first solid electrolyte layer 50d, and the reference electrode 72. In the same manner as in the inner pumping electrode 62 of the main pumping cell 66 described above, the auxiliary pumping electrode 88 is based on the use of a material which has a weak reducing ability or no reducing ability with respect to the NO component in the measurement gas. In this embodiment, for example, the auxiliary pumping electrode 88 is preferably composed of a compound having the perovskite structure such as $La_3CuO_4$, a cermet comprising a ceramic and a metal such as Au having a low catalytic activity, or a cermet comprising a ceramic, a metal of the Pt group, and a metal such as Au having a low catalytic activity. When an alloy composed of Au and a metal of the Pt group is used as an electrode material, it is preferable to add Au in an amount of 0.03 to 35% by volume of the entire metal component.

A desired constant voltage Vp3 is applied between the auxiliary pumping electrode 88 and the reference electrode 72 of the auxiliary pumping cell 90 by the aid of an external DC power source 92. Thus, the oxygen in the atmosphere in the second chamber 60 can be pumped out to the reference gas-introducing space 52.

Accordingly, the partial pressure of oxygen in the atmosphere in the second chamber 60 is controlled to have a low value of partial pressure of oxygen which does not substantially affects the measurement for the amount of the objective component under a condition in which the measurement gas component (NOx) is not substantially reduced or decomposed. In this arrangement, the change in amount of oxygen introduced into the second chamber 60 is greatly reduced as compared with the change in the measurement gas, owing to the operation of the main pumping cell 66 for the first chamber 58. Accordingly, the partial pressure of oxygen in the second chamber 60 is controlled accurately and constantly.

The gas sensor 200 according to this embodiment further comprises a heater 94 for generating heat in accordance with electric power supply from the outside. The heater 94 is embedded in a form of being vertically interposed between the first and second substrate layers 50a, 50b. The heater 94 is provided in order to increase the conductivity of oxygen ion. A ceramic layer 96 composed of alumina or the like is formed to cover upper and lower surfaces of the heater 94 so that the heater 94 is electrically insulated from the substrate layers 50a, 50b.

As shown in FIG. 2, the heater 94 is arranged over the entire portion ranging from the first chamber 58 to the second chamber 60. Accordingly, each of the first chamber 58 and the second chamber 60 is heated to a predetermined temperature. Simultaneously, each of the main pumping cell 66, the controlling oxygen partial pressure-measuring cell 74, and the measuring pumping cell 82 is also heated to a predetermined temperature and maintained at that temperature.

The pumping current, i.e., the offset current, which flows through the measuring pumping cell 82 upon NOx=0, ideally has a value corresponding to the residual oxygen concentration in the first chamber 58 or the auxiliary pumping cell 90. For example, when the oxygen concentration in the first chamber 58 is controlled to be 0.1 ppm by the aid of the main pumping cell 66, the offset current should have a value corresponding to about 0.2 ppm. However, as shown in FIG. 12, the offset current actually has a value corresponding to 200 ppm.

This fact means that 200 ppm of oxygen enters the detecting electrode 80 in any manner. The cause of this phenomenon may be insufficient air-tightness of the second chamber 60 due to incomplete stacking when the sensor element 100 of the gas sensor 200 is produced by sintering a stacked compact of $ZrO_2$ or due to occurrence of microcracks during the sintering process, or insufficient air-tightness of the lead wire (for example, a $Pt/ZrO_2$ cermet lead) connected to the detecting electrode 80 or the auxiliary pumping electrode 88 for making electric connection to the atmospheric side. Surprisingly, it has been revealed that an unexpected portion causes the phenomenon.

Figure 3A:
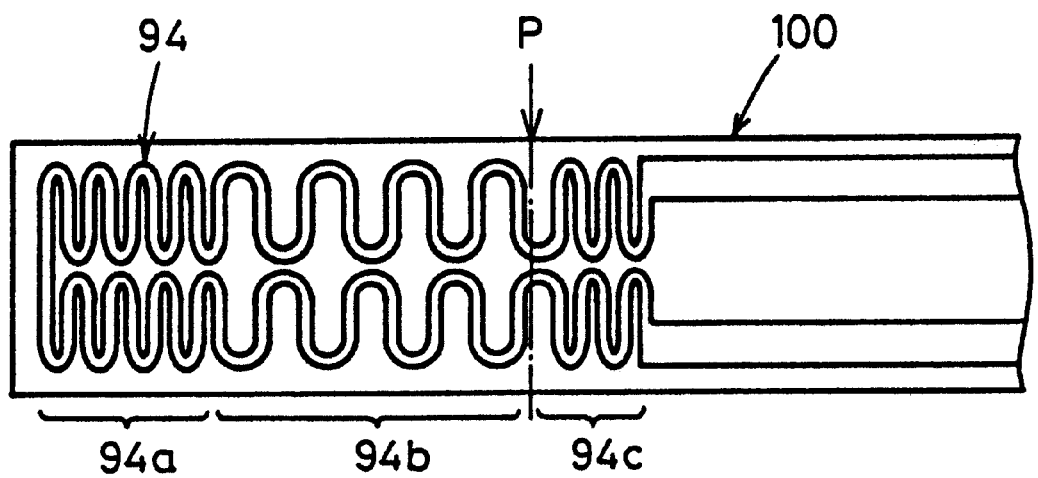
FIG. 3A shows a plan view illustrating a configuration before improvement of the pattern of the heater.
Figure 3B:
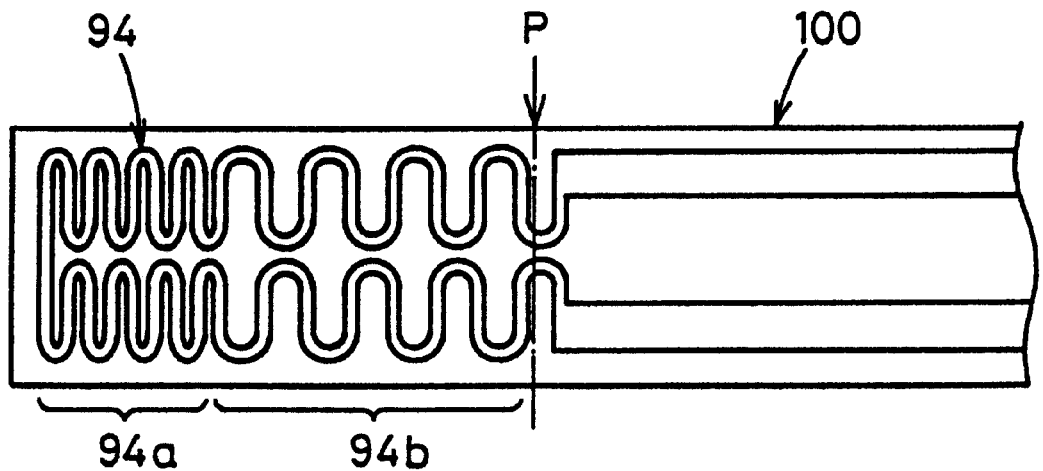
FIG. 3B shows a plan view illustrating a configuration after improvement of the pattern of the heater.
Figure 6:
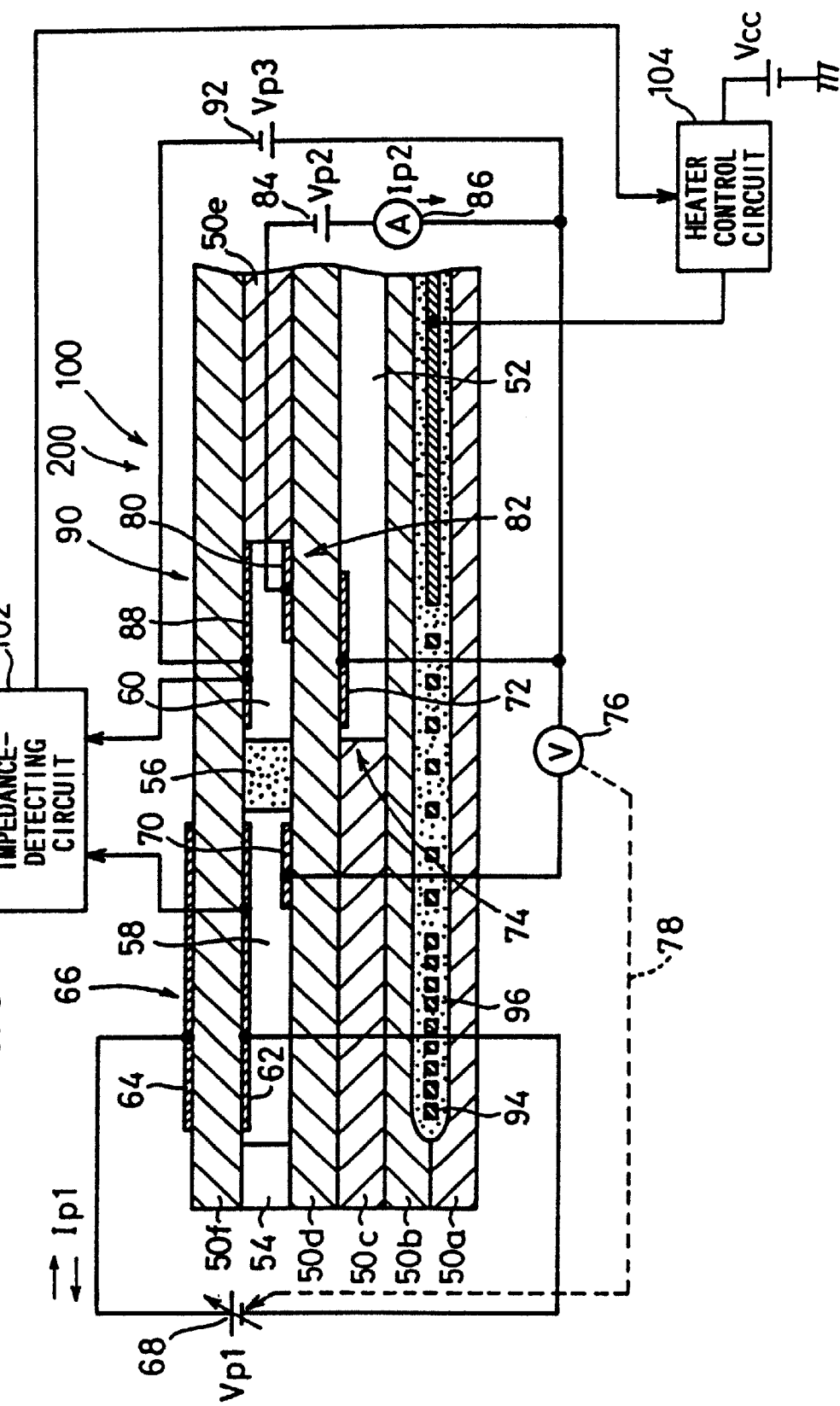
FIG. 6 shows an arrangement of a heater control system provided in the gas sensor according to the embodiment of the present invention together with the sensor element.

In the gas sensor 50 according to the embodiment of the present invention, in order to decrease the offset value, the pattern of the heater 94 is improved as shown in FIG. 3B so that the electronic conduction of the measuring pumping cell 82 is set to be not less than 1 MΩ after conversion into a resistance value.

Specifically, the pattern of the heater 94 is usually devised such that the respective pumping cells 66, 82, 90 are uniformly heated in order to sufficiently bring out the abilities of main pumping cell 66, the measuring pumping cell 82 and the auxiliary pumping cell 90. For example, as shown in FIG. 3A, a minute pitch is used for a pattern 94a at a portion corresponding to the forward end of the sensor element 100, a coarse pitch is used for a pattern 94b at a central portion, and a minute pitch is used for a pattern 94c at a portion corresponding to the backward end of the sensor element 100.

In this embodiment, the temperature between the detecting electrode 80 and the reference electrode 72 of the measuring pumping cell 82, i.e., the temperature at a position (hereinafter simply referred to as "position indicated by Point P") separated from the forward end A of the sensor element 100 by a predetermined distance "m" in the depth direction as shown in FIG. 2 is about 840° C. as shown by a temperature distribution curve "a" in FIG. 4.

On the other hand, as shown in FIG. 3B, the heater 94 of the gas sensor 200 according to the embodiment of the present invention has a pattern in which the pattern 94c of the portion corresponding to the backward end of the sensor element 100 is removed from the pattern of the heater 94 shown in FIG. 3A.

Accordingly, the temperature (temperature at Point P) between the detecting electrode 80 and the reference electrode 72 of the measuring pumping cell 82 is about 700° C. as shown by a temperature distribution curve "b" in FIG. 4. The temperature in this embodiment is lowered by about 140° C. as compared with the temperature of about 840° C. obtained before the improvement of the pattern.

The gas sensor 50 according to the embodiment of the present invention is basically constructed as described above. Next, its function and effect will be explained.

Prior to the measurement of NOx, the gas sensor 200 according to the embodiment of the present invention is set to be in a state in which the measurement gas can be introduced into the first chamber 58. Subsequently, an electric power is applied to the heater 94 to activate the first and second solid electrolyte layers 50d, 50f to be in a desired state.

Next, the measurement gas is introduced into the gas sensor 200 having been set as described above to start measurement of NOx contained in the measurement gas.

The measurement gas is introduced into the first chamber 58 under the predetermined diffusion resistance through the first diffusion rate-determining section 54. The partial pressure of oxygen contained in the measurement gas is controlled to have a predetermined value in accordance with the predetermined pumping voltage Vp1 applied between the inner pumping electrode 62 and the outer pumping electrode 64 by the aid of the variable power source 68. That is, the partial pressure of oxygen in the first chamber 58 can be measured on the basis of the voltage V between the inner pumping electrode 62 and the reference electrode 72 detected by the voltmeter 76. The voltage V is the electromotive force of the oxygen concentration cell specified by the Nernst's equation described above. The voltage of the variable power source 68 is controlled so that the voltage V is, for example, not more than 300 mV. Thus, the partial pressure of oxygen in the first chamber 58 is controlled to have a predetermined value.

The measurement gas, which has been controlled to have the predetermined partial pressure of oxygen in the first chamber 58, is introduced into the second chamber 60 through the second diffusion rate-determining section 56.

In the second chamber 60, the predetermined pumping voltage Vp2, which makes it possible to sufficiently pump out $O_2$ in the second chamber 60, is applied between the reference electrode 72 and the detecting electrode 80 by the aid of the DC power source 84. NOx contained in the measurement gas is decomposed by the aid of the pumping voltage Vp2 or the NOx-decomposing catalyst arranged in the second chamber 60. $O_2$ generated thereby is pumped out toward the reference gas-introducing space 52 through the first solid electrolyte layer 50d. During this process, the current value Ip2, which is generated by the movement of oxygen ion, is measured by the ammeter 86. The concentration of the predetermined oxide, for example, NOx such as NO and $NO_2$ contained in the measurement gas is measured from the current value Ip2.

That is, when the voltage is applied to the oxygen ion-conductive solid electrolyte such as $ZrO_2$ (first solid electrolyte layer 50d in the embodiment shown in FIG. 1), then the current flows in accordance with the movement of oxygen ion, and the current is detected as the pumping current Ip2 by the aid of the ammeter 86. In the case of a proton ion-conductive solid electrolyte, the current flows in accordance with the movement of proton.

When the measuring pumping cell 82 is at a high temperature during the measurement of NOx, the current flowing through the first solid electrolyte 50d includes not only the current originating from oxygen ion. It has been revealed that electronic conduction occurs although it is in an extremely minute amount, and it appears as the offset current.

The electron conductivity is about $1/1000$ as compared with the conductivity of oxygen ion. For example, when it is assumed that the conductivity of oxygen ion corresponds to about $1/100$ (1/Ω), the electronic conduction corresponds (1/(100 k))(1/Ω) which is $1/1000$ thereof. Therefore, the electronic conduction is usually almost neglected.

However, when the gas concentration corresponding to an extremely minute amount is measured, an obtained limiting current is in a degree of only several μA. The electronic conduction at μA level behaves as a large error factor. For example, when the electron conductivity is (1/(100 k))(1/Ω) as described above, application of 0.45 V to the measuring pumping cell 82 gives a large value of the pumping current Ip2=0.45 (V)×(1/(100 k))(1/Ω)=4.5 μA.

When the temperature of the sensor element 100 is changed, and the electron conductivity is changed, for example, it is decreased to ½, then the change in current effected by the electron conduction is changed from 4.5 µA to 2.25 µA. The amount of change is 2.25 µA which is a change corresponding to 500 ppm. Such a change appears as the temperature dependency of the offset value.

In order to decrease the temperature dependency of the offset value, it is necessary to decrease the electron conductivity of the measuring pumping cell 82 as small as possible. However, in the gas sensor 200 according to the embodiment of the present invention, the temperature at Point P in the measuring pumping cell 82 is lowered from 840° C. to 700° C. Therefore, the resistivity of electronic conduction can be raised from 450 kΩ to 4 MΩ after conversion into a resistance value. Thus, the offset value can be lowered from 1 µA to 0.11 µA.

That is, the temperature of the measurement gas is changed, and the temperature change occurs in the sensor element 100. Assuming that the electron conductivity is thereby changed to ½, the offset value is varied in an amount of change of 0.5 µA (corresponding to 100 ppm) before the improvement of the pattern of the heater 94. However, the gas sensor 200 according to the embodiment of the present invention undergoes a slight change of 0.05 µA (corresponding to 10 ppm), making it possible to accurately measure NOx at a low concentration.

FIG. 5 shows such a situation, in which the temperature of the heater 94 is set so that the electronic conduction is 0.2 µA when the temperature of the measurement gas (gas temperature) is 800° C. Even when the gas temperature is changed from 600° C. to 800° C., the offset value changes only in a degree of 0.1 µA. The amount of 0.1 µA corresponds to 20 ppm when conversion is made in view of the sensitivity (5 µA/1000 ppm) of the gas sensor 200. The amount of change is in a satisfactory degree in consideration of the measurement for several hundreds of ppm.

In this embodiment, it is preferable that the heater 94 of the gas sensor 200 is controlled so that the impedance of the auxiliary pumping cell 90 is constant. Description will now be made for a heater control system for controlling the heater 94 to give a constant impedance of the auxiliary pumping cell 90, with reference to FIGS. 6 to 8.

The heater control system comprises an impedance-detecting circuit 102 and a heater control circuit 104. The impedance-detecting circuit 102 is inserted and connected, for example, between the inner pumping electrode 62 and the auxiliary pumping electrode 88 of the main pumping cell 66 except for the detecting electrode 80, for detecting the impedance between the inner pumping electrode 62 and the auxiliary pumping electrode 88. The heater control circuit 104 controls electric power application to the heater 94 on the basis of a detection signal supplied from the impedance-detecting circuit 102.

Figure 7:
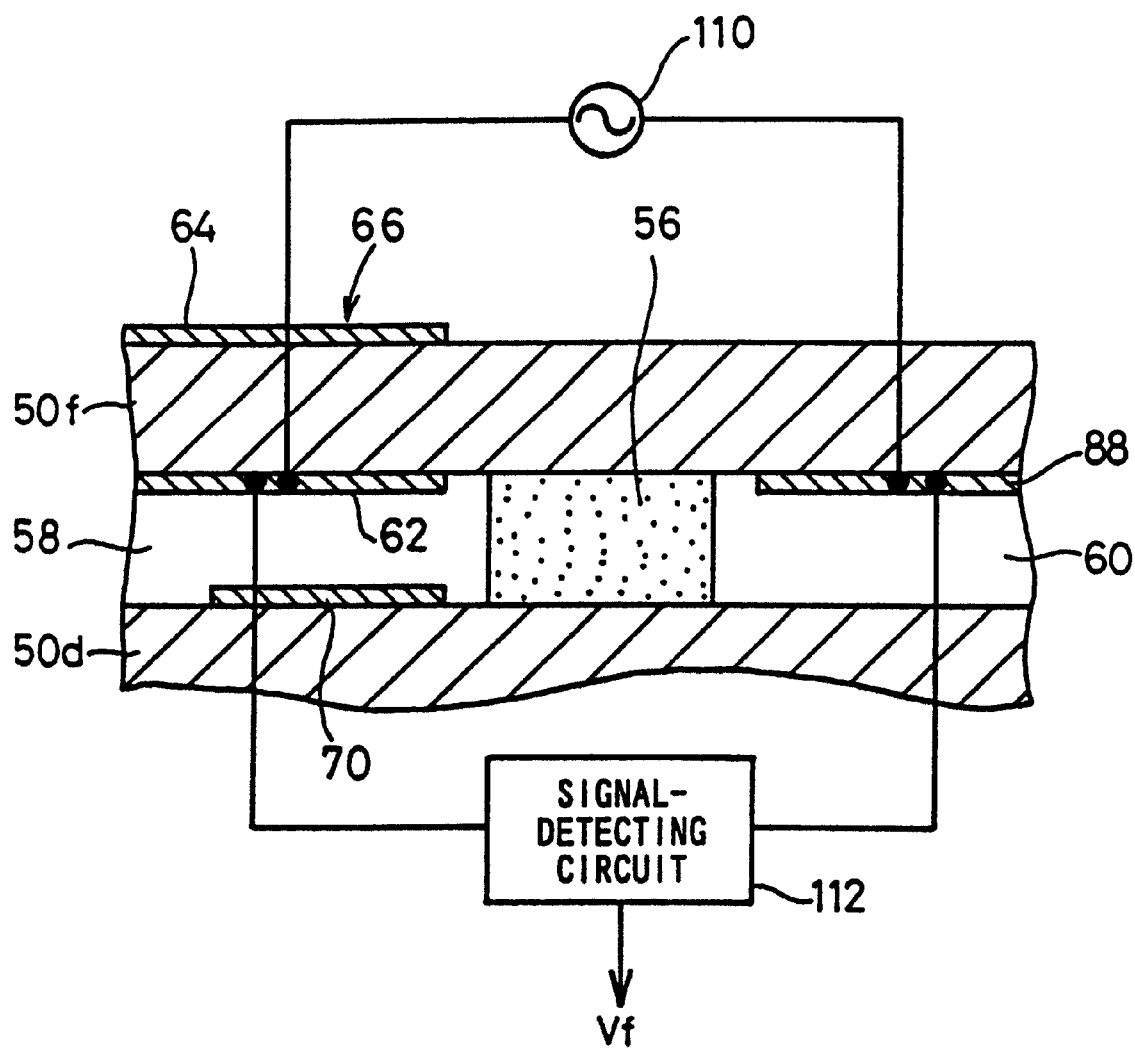
FIG. 7 shows an arrangement of an impedance-detecting circuit of the heater control system.

As shown in FIG. 7, the impedance-detecting circuit 102 comprises an alternating current-generating circuit 110 for supplying an alternating current between the inner pumping electrode 62 and the auxiliary pumping electrode 88, and a signal-detecting circuit 112 for detecting a voltage signal Vf at a level corresponding to the impedance between the inner pumping electrode 62 and the auxiliary pumping electrode 88, generated between the electrodes 62, 88 in accordance with the alternating current supplied between the electrodes 62, 88.

Figure 8:
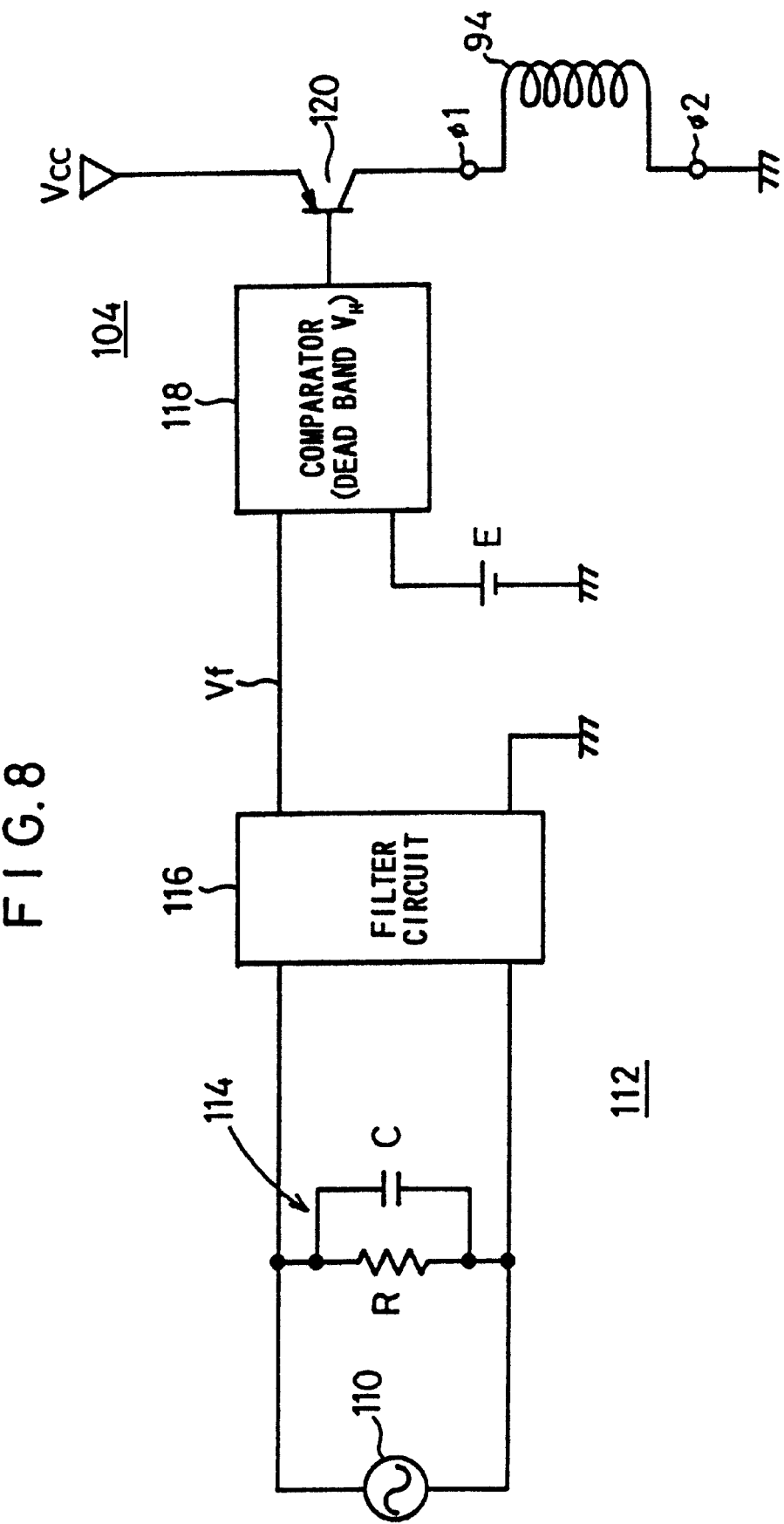
FIG. 8 shows a circuit diagram illustrating an arrangement of the heater control system.

As shown in FIG. 8, the impedance measurement objective, which is constructed by the inner pumping electrode 62, the auxiliary pumping electrode 88, and the second solid electrolyte layer 50f interposed between the both electrodes 62, 88, can be equivalently represented by a circuit 114 in which a resistor R and a capacitor C are connected in parallel.

Therefore, as shown in FIG. 8, the signal-detecting circuit 112 can be constructed by a filter circuit (for example, a low-pass filter or a bandpass filter) 116 for converting the alternating current signal generated between the electrodes 62, 88 into a voltage signal (hereinafter simply referred to as "detection level", if necessary) Vf corresponding to the impedance between the electrodes 62, 88.

As also shown in FIG. 8, the heater control circuit 104 comprises a comparator 118 with hysteresis and a pnp transistor 120. Assuming that the reference level is E, and the dead band level is $V_H$, the comparator 118 with hysteresis outputs a high level signal when the detection level Vf of the voltage signal outputted from the filter circuit 116 is higher than a positive threshold level $(E+V_H/2)$, it outputs a low level signal when the detection level Vf is lower than a negative threshold level $(E-V_H/2)$, and it maintains the present level when the detection level Vf is between $-V_H/2$ and $+V_H/2$.

The pnp transistor 120 has its collector terminal to which a power source Vcc is connected, its base terminal to which an output side of the comparator 118 with hysteresis is connected, and its emitter terminal to which one terminal φ1 of the heater 94 is connected. The other terminal φ2 of the heater 94 is grounded.

The pnp transistor 120 is subjected to ON operation in accordance with the low level signal supplied from the comparator 118 to the base terminal. Accordingly, the driving current is supplied from the power source Vcc to the heater 94. On the other hand, the pnp transistor 120 is subjected to OFF operation in accordance with the high level signal supplied from the comparator 118 to the base terminal. Accordingly, the supply of the driving current to the heater 94 is stopped.

It is desirable that the frequency zone of the alternating current component generated by the alternating current-generating circuit 110 is set to be, for example, within a range of about 300 Hz to 100 kHz. Optimally, the frequency zone is set to be within a range of 1 kHz to 10 kHz. It is desirable that the voltage of the alternating current component is set at a level at which no trouble occurs in the function of each of the electrodes, for example, at a level of not more than 500 mV. Optimally, the voltage is set to be about 100 to 300 mV.

The reference level E supplied to the comparator 118 of the heater control circuit 104 is set to be at the same level as the detection level obtained when the measurement gas temperature in the sensor element 100 is a predetermined temperature (desired temperature).

Next, the operation of the heater control system will be explained. The impedance between the inner pumping electrode 62 and the auxiliary pumping electrode 88 except for the detecting electrode 80 is detected as the voltage level by the aid of the impedance-detecting circuit 102 (see FIG. 6) during the measurement of NOx. The electric power application to the heater 94 is controlled on the basis of the detected voltage level by the aid of the heater control circuit 104.

Specifically, when the gas temperature is increased to be higher than the predetermined temperature, and the impedance between the inner pumping electrode 62 and the auxiliary pumping electrode 88 is increased, then the detection level Vf of the voltage signal, which is outputted from the filter circuit 116 (see FIG. 8) of the impedance-detecting circuit 102, is also becomes high. When the detection level Vf of the voltage signal is higher than the positive threshold level ($E+V_H/2$) of the comparator 118, then the high level signal is supplied to the base electrode of the pnp transistor 120 of the heater control circuit 104, and the electric power application to the heater 94 is stopped. Accordingly, the measurement gas temperature in the sensor element 100 is gradually decreased.

On the other hand, when the gas temperature becomes lower than the predetermined temperature, and the impedance between the inner pumping electrode 62 and the auxiliary pumping electrode 88 is lowered, then the detection level Vf of the voltage signal outputted from the filter circuit 116 also becomes low. When the detection level Vf of the voltage signal is lower than the negative threshold level ($E-V_H/2$) of the comparator 118, then the low level signal is supplied to the base electrode of the pnp transistor 120 of the heater control circuit 104, and the electric power application to the heater 94 is started. Accordingly, the measurement gas temperature in the sensor element 100 is gradually increased. As described above, the temperature in the sensor element 100 can be constantly maintained by controlling the electric power application to the heater 94 on the basis of the impedance value.

When the heater control system is used as described above, the heater 94 is controlled so that the impedance of the auxiliary pumping cell 90 is constant. Alternatively, control may be made so that the impedance of measuring pumping cell 82 is constant. In this alternative embodiment, control is made so that the impedance is constant between the electrodes (between the detecting electrode 80 and the reference electrode 72 in the embodiment shown in FIG. 2) through which the pumping current Ip2 flows. Accordingly, even when the gas temperature is changed from 600° C. to 800° C., the width of change of the offset value is not more than 0.02 $\mu$A (corresponding to 4 ppm). Thus, it is possible to provide the gas sensor 200 having extremely high accuracy.

In the system in which the impedance of the measuring pumping cell 82 is controlled to be constant, it is possible to control the offset value to be constant even when the temperature of the measurement gas is changed. Therefore, the offset value can be easily made to be zero by means of zero adjustment effected on the output side. Accordingly, it is possible to improve the measurement accuracy of the gas sensor 200. Further, the resistivity of electronic conduction of the measuring pumping cell 82 is not less than 100 k$\Omega$ after conversion into a resistance value. Therefore, the gas sensor 200 is advantageous in that sufficient tolerance is obtained (i.e., the offset value can be controlled to be constant) even when the electron conductivity is large to some extent.

A method (procedure) for measuring the electron conductivity of the measuring pumping cell 82 will now be explained. The electron conductivity can be determined by firstly sealing the gas-introducing port of the sensor element 100 with high melting point glass or the like, applying the predetermined pumping voltage (measuring voltage Vp2) to the measuring pumping cell 82 while intercepting supply of oxygen, and measuring the pumping current Ip2 in a state in which no oxygen exists in the space (second chamber) 60.

At an early stage of the voltage application, a large pumping current Ip2 flows, because oxygen remains in the space 60. However, as the oxygen is pumped out, and the oxygen concentration in the space 60 is lowered, the pumping current Ip2 is decreased. The pumping current Ip2 exhibits a constant value at a stage at which no oxygen exists in the space 60. The constant value represents the current caused by the electronic conduction.

The electron conductivity can be determined in accordance with another measuring method. That is, a state is given, in which the oxygen concentration of the measurement gas is approximately zero, for example, about 1 ppm. A voltage, which is in a degree of the electromotive force (electromotive force of the oxygen concentration cell), i.e., about +200 mV between the detecting electrode 80 and the reference electrode 72 of the measuring pumping cell 82, is applied to the measuring pumping cell 82 to measure the pumping current Ip2.

In other words, the limiting current of the measuring pumping cell 82 is, for example, 5 $\mu$A/1000 ppm as described above. In the case of about 0.1 ppm, the limiting current is 1×5/1000=0.005 $\mu$A according to calculation. A value, which is obtained by subtracting the foregoing value from the actually measured current, represent the current value caused by the electronic conduction.

In this case, when the ratio of the current to be subtracted is larger than the value of the current, the error upon calculation is increased. Therefore, in such a case, it is preferable to make measurement while further decreasing the oxygen concentration in the measurement gas.

The method for decreasing the electron conductivity of the measuring pumping cell 82 is not limited to the method for lowering the temperature as described above. The object is achieved by decreasing the area of the detecting electrode 80, or by increasing the purity of the $ZrO_2$ material or the like for constructing the measuring pumping cell 82.

When the area of the detecting electrode 80 of the gas sensor 200 according to the embodiment of the present invention is reduced to ½, the offset value is certainly decreased to ½. The offset value is lowered to 0.5 $\mu$A by increasing the purity of the material for constructing the substrate including the first and second solid electrolyte layers 50$d$, 50$f$ from 96% to 99%, while maintaining the temperature to be ordinary one (temperature indicated by the temperature distribution curve "a" shown in FIG. 4).

The measuring pumping cell 82 is not limited to the oxygen pump constructed by the detecting electrode 80 and the reference electrode 72 provided for the second chamber 60 as shown in FIG. 2. Alternatively, it is also allowable to use an oxygen pump constructed by the detecting electrode 80 an electrode other than the reference electrode 72, and the solid electrolyte intervening between the electrodes. Specifically, the measuring pumping cell 82 can be constructed, for example, by an oxygen pump constructed by the detecting electrode 80 for the second chamber 60 and the inner pumping electrode 62 of the main pumping cell 66, an oxygen pump constructed by the detecting electrode 80 for the second chamber 60 and the outer pumping electrode 64 of the main pumping cell 66, or an oxygen pump constructed by the detecting electrode 80 for the second chamber 60 and an electrode provided separately on the element surface on the exhaust gas side. In these arrangements, a system is adopted, in which the pumping current Ip2 is allowed to flow between the detecting electrode 80 and the electrode (the inner pumping electrode 62, the outer pumping electrode 64, or the electrode provided separately on the element surface on the exhaust gas side) other then the reference electrode 72, while monitoring the electromotive force (electromotive force of the oxygen concentration cell) generated between the reference electrode 72 and the detecting electrode 80.

In any of the arrangements, in short, the electron conductivity of the pumping cell through which the pumping current Ip2 to be measured flows is decreased to an extent that the electron conductivity is negligible as compared with the ion current generated by the decomposition of the gas component to be measured.

Especially, when the heater 94 is controlled so that the impedance of the measuring pumping cell 82 is constant, the impedance is measured between the detecting electrode 80 and the electrode (the inner pumping electrode 62, the outer pumping electrode 64, or the electrode provided separately on the element surface on the exhaust gas side) other then the reference electrode 72 through which the pumping current Ip2 flows. The control system may be constructed so that the heater 94 is controlled on the basis of the result of the measurement.

An advantage is obtained in that the effect obtained by the system for controlling the impedance of the measuring pumping cell 82 to be constant is larger than the effect obtained by the improvement of the configuration of the heater pattern or by the reduction of the area of the detecting electrode 80 as described above.

Figure 9:
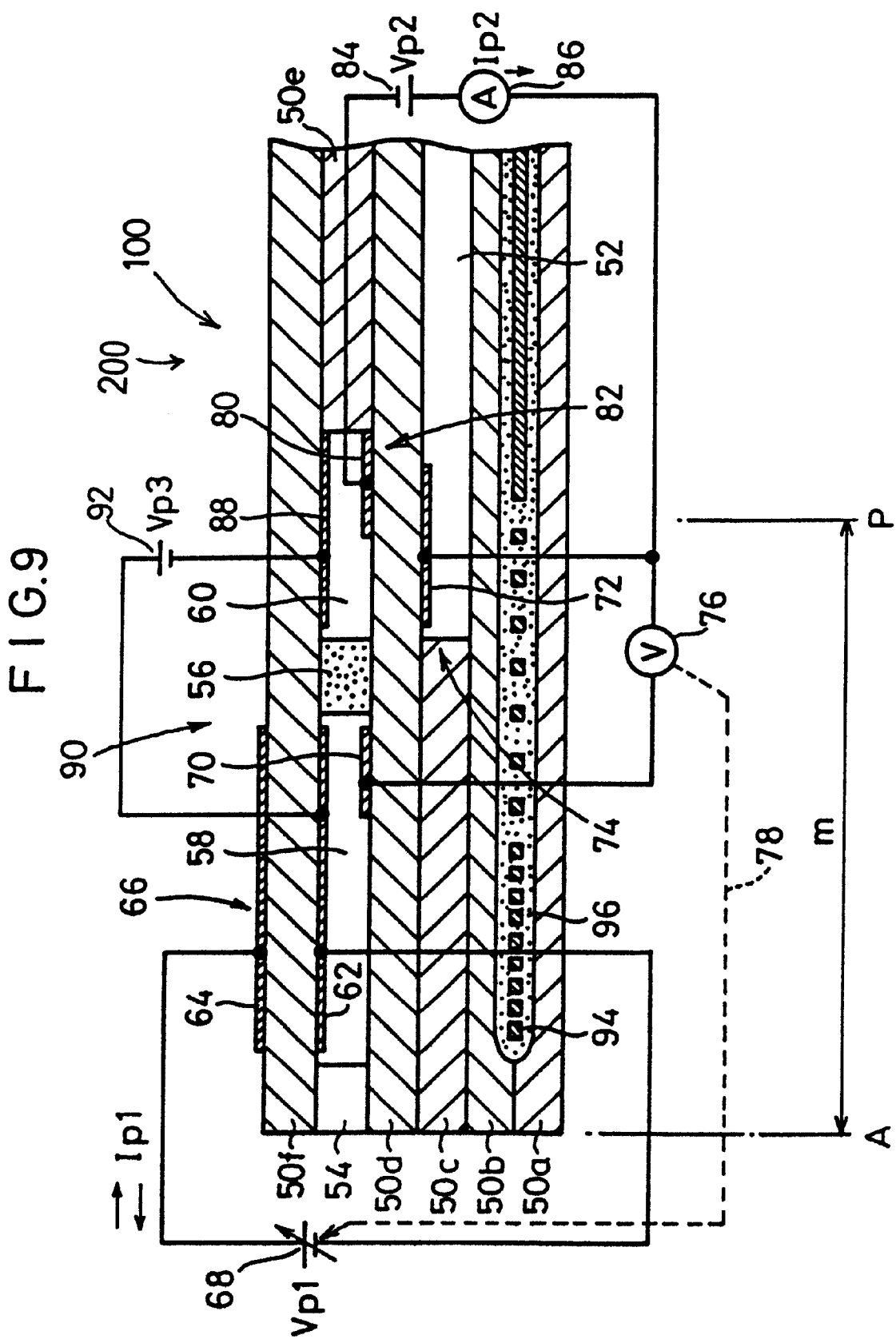
FIG. 9 shows another illustrative arrangement of an auxiliary pumping cell.
Figure 10:
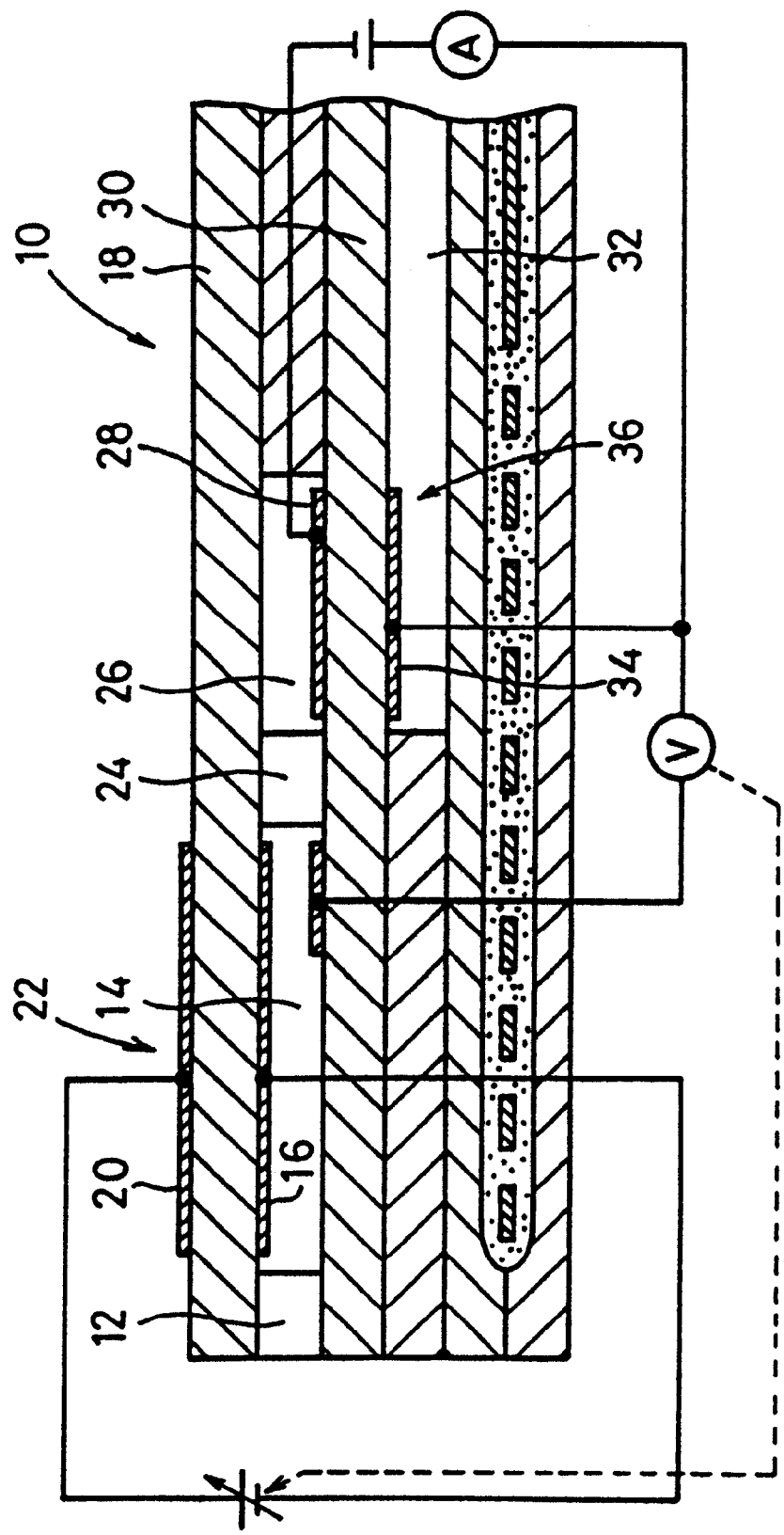
FIG. 10 shows an arrangement of a suggested conventional gas sensor.
Figure 11:
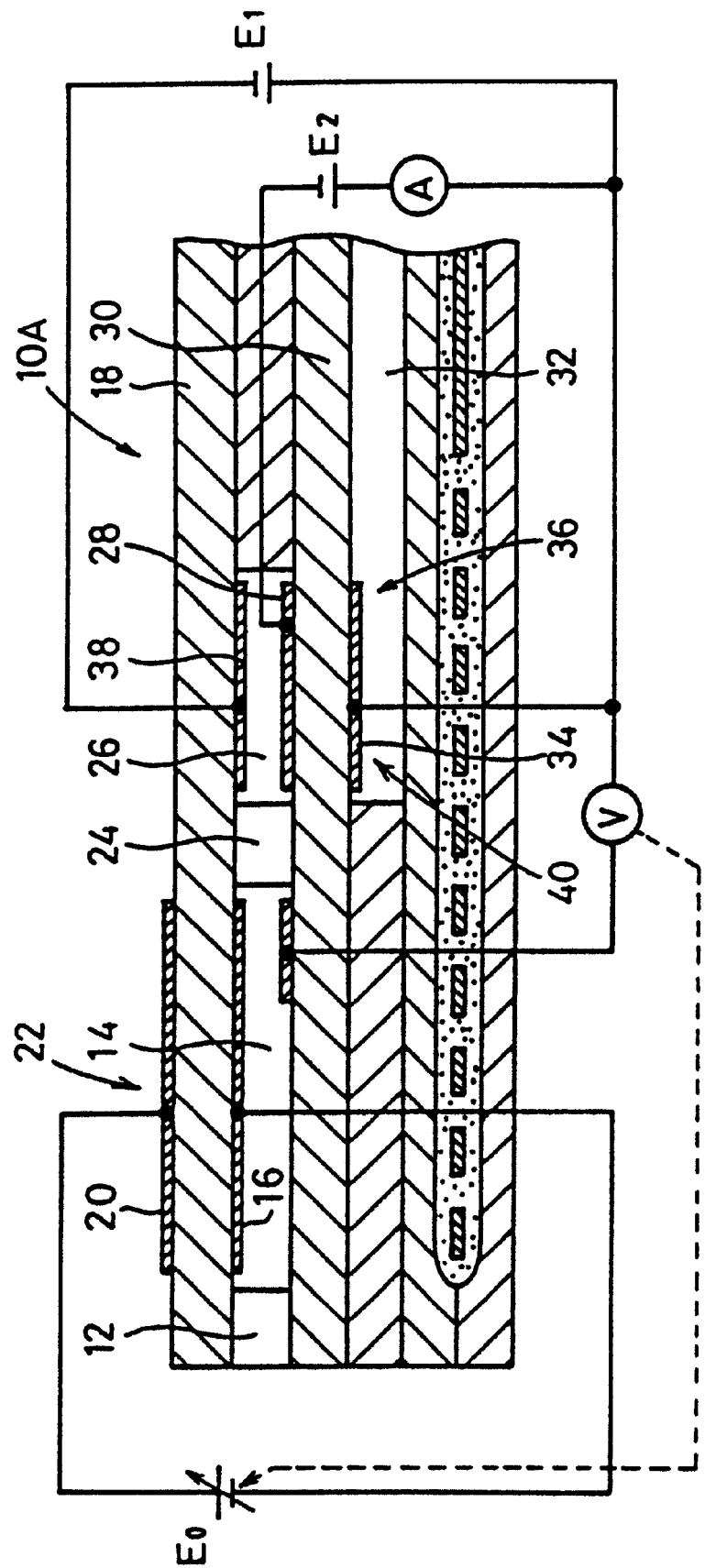
FIG. 11 shows an arrangement of another suggested conventional gas sensor.
Figure 13:
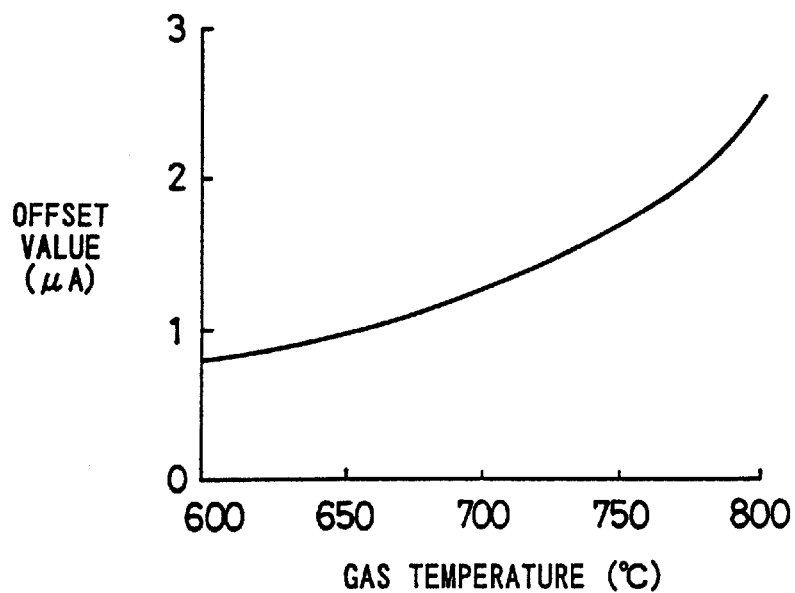
FIG. 13 shows a characteristic curve illustrating the variation of offset value with respect to the change in gas temperature in the suggested conventional gas sensor.

Alternatively, as shown in FIG. 9, the oxygen in the atmosphere in the second chamber 60 may be pumped out into the first chamber 58 by constructing the auxiliary pumping cell 90 with the auxiliary pumping electrode 88 provided in the second chamber 60, the second solid electrolyte layer 50f, and the inner pumping electrode 62 of the main pumping cell 66.

As described above, according to the gas sensor 200 concerning the embodiment of the present invention, the resistivity of electronic conduction of the measuring pumping cell 82 is set to be not less than 1 MΩ after conversion into a resistance value. Therefore, it is possible to suppress the electronic conduction which would be otherwise caused in the measuring pumping cell 82. Accordingly, it is possible to decrease the offset value. Thus, the gas sensor 200 according to the embodiment of the present invention is extremely useful to measure NOx at a low concentration.

As described above, in the gas sensor 200 according to the embodiment of the present invention, the electron conductivity of the measuring pumping cell 82 is not less than 1 MΩ after conversion into a resistance value. However, the electron conductivity is preferably not less than 2 MΩ, and more preferably not less than 4 MΩ. However, in the case of the system in which the impedance of the measuring pumping cell 82 is controlled, a sufficient effect is obtained even when the resistivity of electronic conduction of the measuring pumping cell 82 is not less than 100 kΩ.

The pumping ability of the measuring pumping cell 82 is lowered when the temperature in the vicinity of the measuring pumping cell 82 is lowered or when the area of the detecting electrode 80 is reduced, in order to decrease the electronic conduction of the measuring pumping cell 82. However, the pumping ability may be set to have a value which is about two times the limiting value of the pumping ability.

For example, when it is intended to measure a concentration of 1000 ppm at maximum, the temperature in the vicinity of the measuring pumping cell 82 is gradually lowered at a gas concentration of 2000 ppm. The temperature, at which the decrease in sensitivity begins to occur, is set to be the limiting temperature/limiting area. By doing so, it is possible to design a pump which has an enough margin for the measurement for 1000 ppm.

When the temperature of the gas sensor 200 is controlled, it is preferable to control the heater 94 while monitoring the temperature of the measuring pumping cell 82, because of the following reason. That is, the offset value is controlled to be constant, because the electron conductivity is controlled to be constant even when the exhaust gas temperature is changed. In this case, an alternating current may be applied to measure the alternating current impedance of the measuring pumping cell 82. Alternatively, a small voltage, at which current limiting does not occur, may be intermittently applied to the measuring pumping cell 82 to measure the direct current impedance. Further alternatively, another temperature-measuring means may be provided in the vicinity of the measuring pumping cell 82.

The gas sensor 200 according to the embodiment of the present invention is directed to NOx as the predetermined gas component to be measured. However, the gas sensor of the present invention is effectively applicable to the measurement of bound oxygen-containing gas components such as $H_2O$ and $CO_2$ other than NOx, which is affected by oxygen existing in the measurement gas.

The gas sensor of the present invention is also applicable to gas sensors constructed to pump out, with an oxygen pump, $O_2$ produced, for example, by electrolysis of $H_2O$ and $CO_2$, and gas sensors for pumping-processing $H_2$ produced by electrolysis of $H_2O$ by using a proton ion-conductive solid electrolyte.

It is a matter of course that the gas sensor according to the present invention is not limited to the foregoing embodiments, which may be constructed in other various forms without deviating from the gist or essential characteristics of the present invention.

As described above, the gas sensor according to the present invention makes it possible to decrease the offset value to an extent that no trouble occurs in the measurement, without causing any reduction of NOx, and thus it is possible to improve the measurement accuracy for the predetermined gas component.

What is claimed is:

1. A gas sensor comprising:

a main pumping means for pumping-processing oxygen contained in a measurement gas introduced from an external space into a processing space defined by a first chamber formed by solid electrolytes contacting with said external space so that a partial pressure of oxygen in said processing space is controlled to have a predetermined value at which a predetermined gas component contained in said measurement gas is not decomposable;

a measuring pumping means for decomposing a measurement gas component contained in said measurement gas introduced from said first chamber into another processing space defined by a second chamber, after being pumping-processed by said main pumping means, by means of catalytic action and/or electrolysis so that oxygen produced by said decomposition is subjected to a pumping process; and a heater for heating at least said main pumping means and said measuring pumping means to predetermined respective temperatures, said heater having a serpentine pattern extending across said first and second chambers, said pattern having a pitch which is wider at one end, across a region adjacent said second chamber, than at another end thereof, so that the temperature of said measuring pumping means is lower than the temperature of said main pumping means:

wherein:

said measurement gas component contained in said measurement gas is measured on the basis of a pumping current allowed to flow through said measuring pumping means in accordance with said pumping process effected by said measuring pumping means; and said measuring pumping means has a resistivity of electronic conduction of not less than 1 MΩ after conversion into a resistance value and not more than about 20 MΩ.

2. The gas sensor according to claim 1, wherein said predetermined gas component is NO, and said measurement gas component is NOx.

3. The gas sensor according to claim 1, wherein said resistivity of electronic conduction of said measuring pumping means is not less than 2 MΩ after conversion into a resistance value.

4. The gas sensor according to claim 3, wherein said resistivity of electronic conduction of said measuring pumping means is not less than 4 MΩ after conversion into a resistance value.

5. The gas sensor according to claim 1, further comprising an auxiliary pumping means including said solid electrolyte and an inner auxiliary pumping electrode and an outer auxiliary pumping electrode formed in contact with said solid electrolyte, for pumping out oxygen contained in said measurement gas after being pumping-processed by said main pumping means, toward said main pumping means.

6. The gas sensor according to claim 1, further comprising heater control means for controlling electric power of said heater so that said temperature in the vicinity of said measuring pumping means is constant.

7. The gas sensor according to claim 1, further comprising heater control means for controlling electric power of said heater so that said measuring pumping means has a constant impedance.

* * * * *